United States Patent
Jew et al.

(10) Patent No.: US 6,274,559 B1
(45) Date of Patent: Aug. 14, 2001

(54) LIVER PROTECTION OR TREATMENT AGENTS COMPRISING ASIATIC ACID DERIVATIVES AS THE ACTIVE COMPONENT

(75) Inventors: Sang Sup Jew; Hyeung Geun Park; Hee Doo Kim, all of Seoul; Young Hoon Jung, Kyunggi-do; Young Choong Kim, Seoul; Hong Pyo Kim, Seoul; Mi Kyeong Lee, Seoul; Hee Sung Choi, Seoul; Eung Seok Lee, Seoul; Chi Hyoung Yoo, Pusan; Doo Yeon Lim, Seoul; Jeong Hoon Kim, Seoul; Hee Man Kim, Seoul, all of (KR)

(73) Assignee: Dong Kook Pharmaceutical Co., Ltd. (KR)

( * ) Notice: Subject to any disclaimer, the term of this patent is extended or adjusted under 35 U.S.C. 154(b) by 0 days.

(21) Appl. No.: 09/380,100

(22) PCT Filed: Feb. 28, 1998

(86) PCT No.: PCT/KR98/00038

§ 371 Date: Aug. 27, 1999

§ 102(e) Date: Aug. 27, 1999

(87) PCT Pub. No.: WO98/37899

PCT Pub. Date: Sep. 3, 1998

(30) Foreign Application Priority Data

Feb. 28, 1997 (KR) .................................................. 97/6655

(51) Int. Cl.⁷ .................................................. A61K 31/00
(52) U.S. Cl. .............................. 514/26; 514/25; 514/893; 514/894; 536/5
(58) Field of Search .................... 536/5; 514/26, 514/25, 893, 894

(56) References Cited

U.S. PATENT DOCUMENTS

| | | | |
|---|---|---|---|
| 5,834,437 | * 11/1998 | Jew et al. | 514/25 |
| 6,017,898 | * 6/2000 | Jew et al. | 514/169 |

FOREIGN PATENT DOCUMENTS

| | | |
|---|---|---|
| 0 197 525 A2 | 10/1986 | (EP) . |
| 0 383 171 A2 | 8/1990 | (EP) . |
| 2 174 904 | 11/1986 | (GB) . |
| 64-39973 | 2/1989 | (JP) . |
| 3-287530 | 12/1991 | (JP) . |
| 96/17819 | * 6/1996 | (WO) . |
| 97/03088 | * 1/1997 | (WO) . |
| 97/31014 | * 8/1997 | (WO) . |
| 98/23278 | * 6/1998 | (WO) . |
| 98/23574 | * 6/1998 | (WO) . |

OTHER PUBLICATIONS

Balanehru, S. et al., "Intervention of Adriamycin induced free radical damage," *Chem Abstr*, 118:73273f (1993).

Shukla, B. et al., "Hepatoprotective activity in the rat of ursolic acid isolated from Eucalyptus hybrid," *Chem Abstr.*, 117:205146e (1992).

Balanehru, S. et al., "Protective effect of oleanolic acid and ursolic acid against lipid peroxidation," *Chem Abstr.*, 116:345e (1992).

Gan, K. H. et al., "Studies on the constituents of Formosan gentianaceous plants. Part XI. Constituents of Gentiana flavo–maculata and Tripterospermum taiwanense and the antihepatotoxic activity of ursolic acid derivatives," *Chem Abstr.*, 110:132213w (1989).

Ma, X. et al., "Preventive and therapeutic effects of ursolic acid (UA) on acute liver injury in rats," *Chem Abstr.*, 105:72646z (1986).

Saponins. Ed. by Hostettmann and Marston. Cambridge Univ. Press, pp. 273 and 324–325, 1995.*

Kasai et al. "Saponins", (Ch. 9 of Naturally Occurring Glycosides, ed. by Ikan), John Wiley & Sons, pp. 295–309, 1999.*

* cited by examiner

Primary Examiner—Ralph Gitomer
Assistant Examiner—Devesh Khare
(74) Attorney, Agent, or Firm—Heslin & Rothenberg, PC

(57) ABSTRACT

Compositions and methods of treating or preventing hepatotoxicity utilizing asiatic acid derivatives of Formula 1 are disclosed.

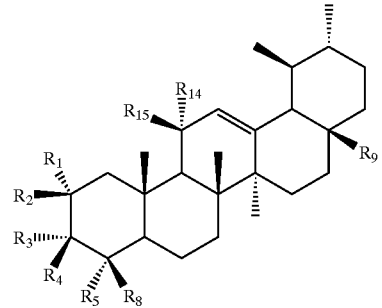

3 Claims, No Drawings

LIVER PROTECTION OR TREATMENT AGENTS COMPRISING ASIATIC ACID DERIVATIVES AS THE ACTIVE COMPONENT

PRIOR FOREIGN APPLICATIONS

This application is a 35 USC §371 filing of PCT/KR98/00038, filed Feb. 28, 1998 and claims priority from KR patent application number 1997/6655, filed Feb. 28, 1997.

TECHNICAL FIELD

The present invention relates to liver protection or treatment agents, which comprise asiatic acid derivatives having the following formula 1:

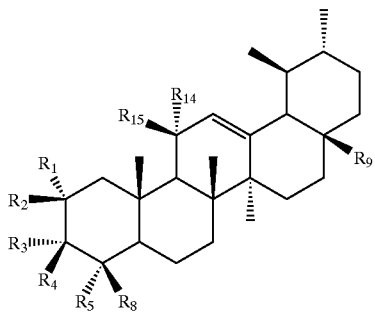

wherein, $R_1$ represents hydrogen, hydroxyl group which may be protected by acetyl or benzyl group, methyl, ethyl, methoxy, ethoxy, vinyl, ethinyl, cyano, azide, ethoxymethyloxy, octyloxymethyloxy, methanesulfonyloxy, phenylthio group or (methylthio)thiocarbonyloxy group; $R_2$ represents hydrogen or hydroxyl group which may be protected by acetyl or benzoyl group, methoxy or ethoxy group; $R_1$ and $R_2$ may form an oxo group; $R_3$ represents hydrogen, hydroxyl group which may be protected by acetyl or benzoyl group, vinyl, methyl or ethyl group; $R_4$ represents hydrogen, methyl, ethyl, vinyl, or hydroxyl group which may be protected by acetyl or benzoyl group; $R_2$ and $R_4$ may form an epoxy group; $R_3$ and $R_4$ may form an oxo group; $R_5$ represents methyl, hydroxymethyl group of which hydroxyl group may be protected by acetyl or benzoyl group, tert-butyldimethylsilyloxymethyl group, carboxylic group, carboxylic ester moiety, carboxylic amide moiety or aldehyde group; $R_4$ and $R_5$ may form —$OCR_6R_7OCH_2$— [wherein, $R_6$ is hydrogen, a lower alkyl group having 1 to 4 carbon atoms, or phenyl group, $R_7$ represents hydrogen, a lower alkyl group having 1 to 4 carbon atoms or phenyl group, and $R_6$ and $R_7$ may form —$(CH_2)_5$—]; $R_8$ represents hydrogen or methyl group; $R_9$ represents —$CH_2COOR$ or —COOR [wherein, R represents hydrogen, a lower alkyl group having 1 to 4 carbon atoms, 2-tetrahydropyranyl, $CH(OR_{11})R_{10}$, $CH(OR_{13})CH_2R_{12}$ (wherein, $R_{10}$ represents hydrogen, methyl or ethyl group, $R_{11}$ represents a lower alkyl group having 1 to 4 carbon atoms, octyl, benzyl, methoxymethyl or methoxyethyl group, $R_{12}$ represents hydrogen, methyl or ethyl group, $R_{13}$ represents methyl or ethyl group, or $R_{12}$ and $R_{13}$ may form —$CH_2CH_2CH_2$—), or glucosyl or rhamnosyl group], hydroxymethyl of which hydroxyl group may be protected by acetyl or benzoyl group, methanesulfonyloxymethyl or cyanomethyl group; $R_{14}$ and $R_{15}$ independently represent hydrogen, or both form oxo group together [provided that when $R_1$ is hydroxyl, $R_2$ is hydrogen, $R_3$ is hydrogen, $R_4$ is hydroxyl, $R_5$ is hydroxymethyl and $R_8$ is methyl, R does not represent hydrogen nor methyl, and Rio does not represent hydrogen; and provided that when $R_1$ is hydroxyl, $R_2$ is hydrogen, $R_3$ or $R_4$ may form, with $R_5$—OC$(R_6)(R_7)OCH_2$—, and $R_6$ is methyl, R does not represent methyl group;

or pharmaceutically acceptable salts or esters thereof, as the active component.

BACKGROUND ART

Asiatic acid, madecassic acid and asiaticoside, trisaccharide of asiatic acid, which are compounds extracted from *Centella asiatica*, isolated firstly by Bontems in 1941 [J. E. Bontems, *Bull. Sci. Pharmacol.*, 49, 186–91(1941)] and their structures were defined by Polonsky [J. Polonsky, *Compt. Rend.*, 232, 1878–80(1951); J. Polonsky, *Bull. Soc. Chim.*, 173–80(1953)].

The extracts including asiatic acid and asiaticoside from *Centella asiatica* have been used for treatment of hurted skin or chronic ulcer since old times, and also for treatment deformation of skin due to tuberculosis or leprosy [P. Boiteau, A. Buzas, E. Lederer and J. Polonsky, *Bull. Soc. Chim.*, 31, 46–51(1949)].

DISCLOSURE OF THE INVENTION

The present inventors have already synthesized various asiatic acid derivatives represented by the formula 1 as above and filed with the Korea Industrial Property Office as a patent application (Korean patent laid-open publication No. 96-22435, Korean Patent Application No. 96-58175), and also performed intensive studies on the asiatic acid derivatives, and found the fact that the derivatives of the formula are useful for liver protection or treatment, to complete the invention.

The object of the present invention is to provide liver protection or treatment agents, which comprise asiatic acid derivatives of the formula 1 as the active component:

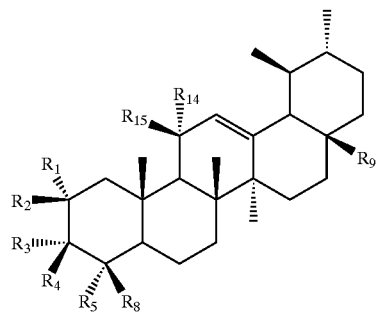

(wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are the same that are defined above.)

Specific examples of the compounds of the above formula 1 include 2-oxoasiatic acid, 2-methylasiatic acid, methyl 2α-acetoxyurs-12-en-23-al-3-on-28-oate, tetrahydropyranyl 3 β,23-diacetoxyurs-12-en-28-oate, ethoxymethyl 2α-hydroxy-3 β,23-isopropylidendioxyurs-12-en-28-oate,
methyl 2,3-β-epoxy-12-en-23-carbomethoxyurs-28-oate,
methyl 2,3-β-epoxy-12-en-23-benzamidours-28-oate,
1-ethoxyethyl asiatate, 2',3',4',6'-tetra-O-acetylglucosyl 2,3,
23-tri-O-acetylurs-28-oate, etc.

The liver protection or treatment agents of this invention may comprise pharmaceutically acceptable salts or esters of the above active components.

The general preparation of the compounds of the formula 1 according to the present invention is presented by Korean patent laid-open publication No. 96-22435, and for the compounds of the formula 1 which can be defined as the formula 2 below, it is desirable to prepare by Method 1~8.

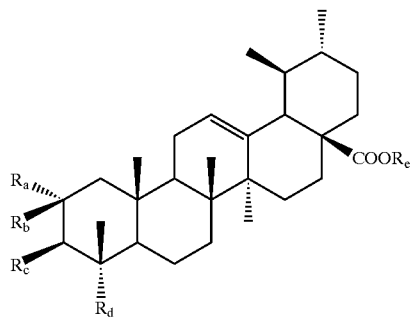

wherein, $R_a$ represents hydrogen, hydroxyl group which may be protected by acetyl or benzyl group, methanesulfonyloxy, (methylthio) thiocarbonyloxy, halogen, ethoxymethyloxy or octyloxymethyloxy group; $R_b$ represents hydrogen or hydroxyl group; $R_a$ and $R_b$ may form an oxo group; $R_c$ represents hydrogen or hydroxyl group which may be protected by acetyl or benzoyl group; $R_b$ and $R_c$ may form an epoxy group; $R_d$ represents hydroxymethyl group which may be protected by acetyl or benzoyl group; $R_c$ and $R_d$ may form —OC($R_f$)($R_g$)OCH$_2$— [wherein, $R_f$ is hydrogen, a lower alkyl group having 1 to 4 carbon atoms, or phenyl group, $R_g$ represents hydrogen, a lower alkyl group having 1 to 4 carbon atoms or phenyl group, and $R_f$ and $R_g$ may form —(CH$_2$)$_5$—]; $R_e$ represents hydrogen, a lower alkyl group having 1 to 4 carbon atoms, an alkoxymethyl group having 1 to 4 carbon atoms, octyloxymethyl, methoxyethoxymethyl, benzyloxymethyl or 2-tetrahydropyranyl group The preparations of asiatic acid derivatives of the formula 2 above according to the present invention are presented below.

Method 1

Titrated extracts of *Centella asiatica* (TECA) is hydrolyzed to obtain a mixture of asiatic acid and madecassic acid, and the mixture is reacted with 2,2-dimethoxypropane in the presence of acid catalyst. The reaction product is purified by column chromatography to isolate 3,23-O-isopropylidene asiatic acid (3) in which 3,23-dihydroxy group is protected. The obtained product is treated with diazomethane to synthesize methyl 3,23-O-isopropylidene asiatate (4). [See Scheme 1.]

Scheme 1

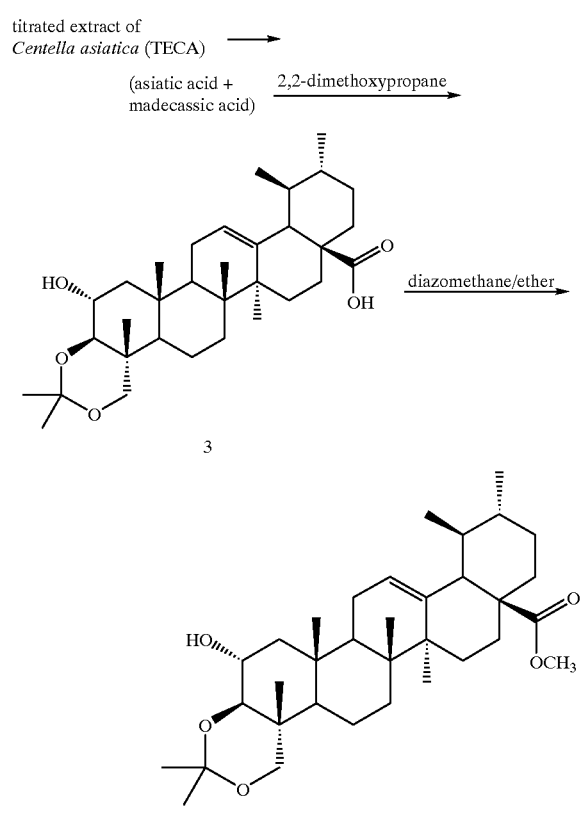

Method 2

Two hydroxyl groups at 3- and 23-position of asiatic acid are protected with various ketone or aldehyde group to synthesize compounds represented by formula 5. [Provided that $R_f$=H and $R_g$=H, the compound is synthesized by the use of dimethyl sulfoxide and trimethylsilyl chloride.] The compound of the formula 5 is treated with chloromethyl octyl ether to synthesize a compound represented by the formula 6. [See Scheme 2.]

Scheme 2

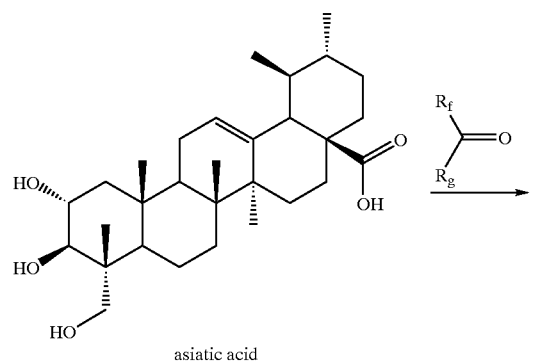

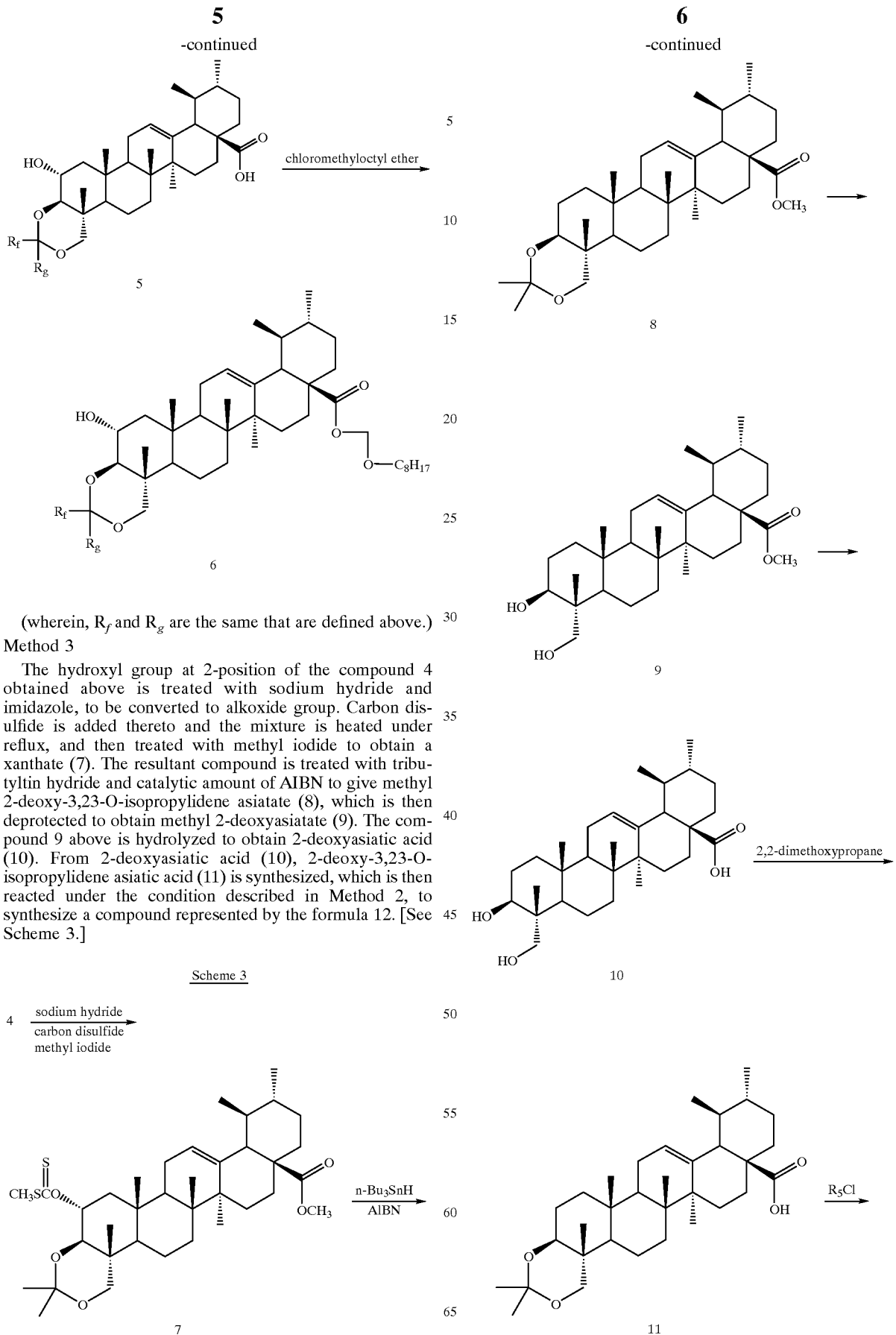

(wherein, $R_f$ and $R_g$ are the same that are defined above.)

Method 3

The hydroxyl group at 2-position of the compound 4 obtained above is treated with sodium hydride and imidazole, to be converted to alkoxide group. Carbon disulfide is added thereto and the mixture is heated under reflux, and then treated with methyl iodide to obtain a xanthate (7). The resultant compound is treated with tributyltin hydride and catalytic amount of AIBN to give methyl 2-deoxy-3,23-O-isopropylidene asiatate (8), which is then deprotected to obtain methyl 2-deoxyasiatate (9). The compound 9 above is hydrolyzed to obtain 2-deoxyasiatic acid (10). From 2-deoxyasiatic acid (10), 2-deoxy-3,23-O-isopropylidene asiatic acid (11) is synthesized, which is then reacted under the condition described in Method 2, to synthesize a compound represented by the formula 12. [See Scheme 3.]

Scheme 3

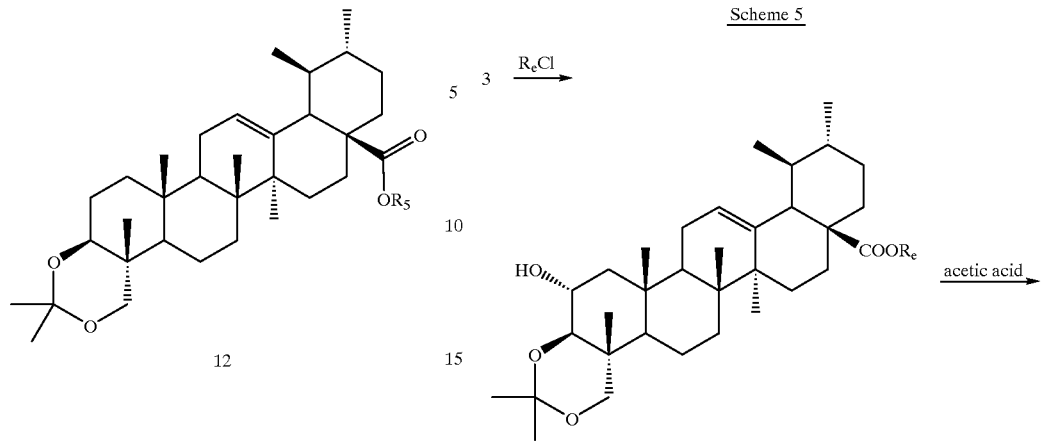

12

Method 4

Methyl 2-O-octyloxymethyl-3,23-O-isopropylidene asiatate (13) is synthesized by means of Method 2 from the compound 4 obtained above. [See Scheme 4.]

Scheme 4

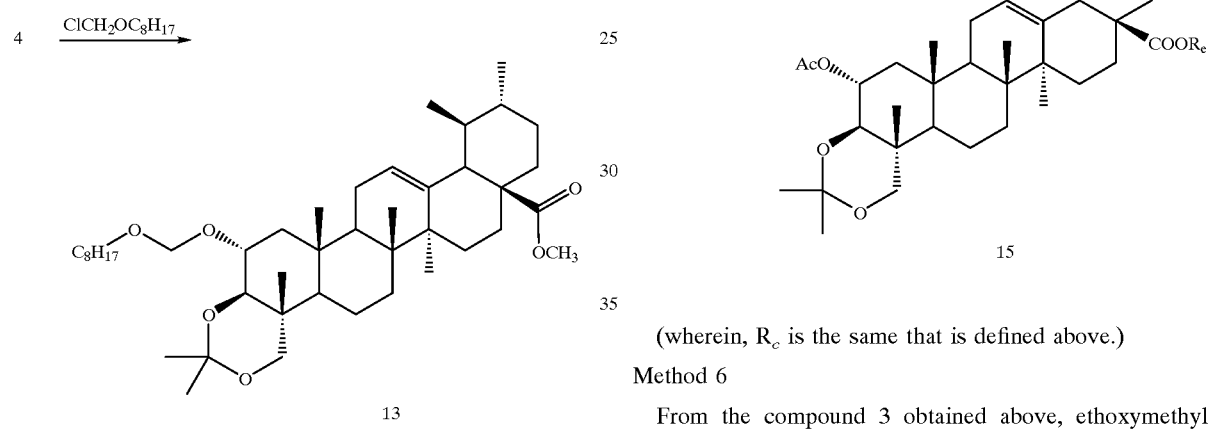

13

Method 5

The compound 3 obtained above is reacted with an alkyl halide under the conditions of Method 2, to synthesize a compound represented by the formula 14, which is acetylated at 2-position to synthesize a compound represented by the formula 15. [See Scheme 5.]

Scheme 5

14

15

(wherein, $R_c$ is the same that is defined above.)

Method 6

From the compound 3 obtained above, ethoxymethyl 2-O-ethoxymethyl-3,23-0-isopropylidene asiatate (16) is obtained under the same conditions of Method 2 but with prolonged reaction time. By means of the same method, benzyloxymethyl group is incorporated to COOH group at 28-position by using chloromethyl benzyl ether. The resultant compound is acetylated to synthesize benzyloxymethyl 3,23-O-diacetylasiatate (17). [See Scheme 6.]

Scheme 6

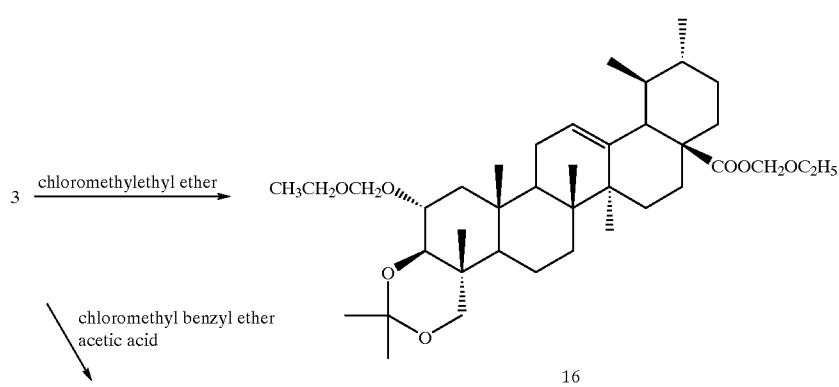

16

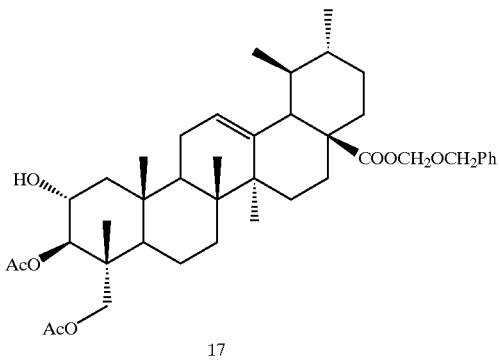

Method 7

2,3-Hydroxy group of asiatic acid is converted to 2,3-epoxy group, and the obtained compound is reacted with a variety of nucleophilic compound to cause ring opening of epoxy group to prepare a series of novel compounds according to the present invention. In other words, the compound 4 obtained above is reacted with methanesulfonyl chloride to obtain methyl 2-O-methanesulfonyl-3,23-O-isopropylidene asiatate (18), which is then treated with PTSA to give methyl 2-O-methanesulfonyl asiatate (19). The obtained compound is then treated with potassium carbonate in methanol solvent to synthesize methyl 2,3-epoxyasiatate (20). The compound 20 is treated with lithium iodide trihydrate and acetic acid to synthesize methyl 2-α-iodo-2-deoxyasiatate (21) of which epoxide has been opened. [See Scheme 7.]

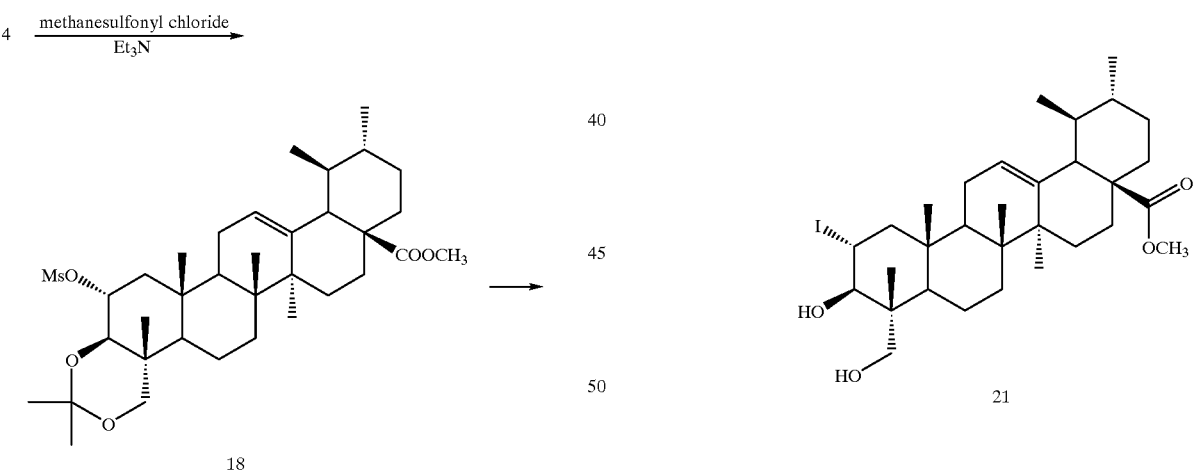

Method 8

Dihydroxy group at 3- and 23-position of asiatic acid was methylidene protected by dimethylsulfoxide and trimethylsilyl chloride to synthesize a compound represented by the formula (5, $R_f=R_g=H$), which is then treated with pyridinium dichromate (PDC) to obtain a compound represented by the formula 22. The resultant compound is reacted with chloromethyl octyl ether to give a compound represented by the formula 23. [See Scheme 8.]

Scheme 8

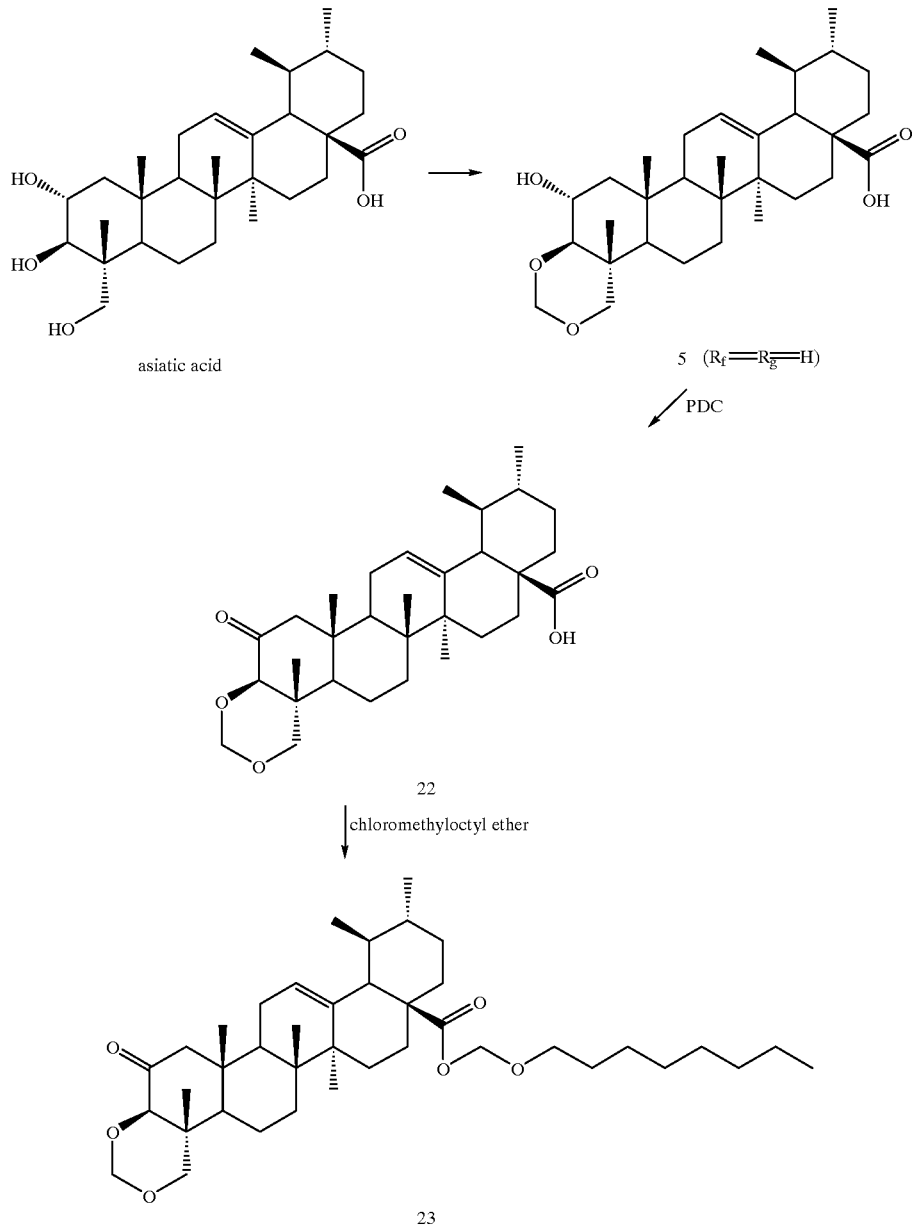

The dose of the compound of the formula 1 is 0.05 to 150 mg/day for an adult. The dose usually varies depending on age and body weight of a patient, as well as the condition of symptoms.

The liver protection or treatment agents according to the present invention may be formulated into a suitable formulation for oral or parenteral administration by using conventional methods. For oral administration, it may be formulated as tablets, capsules, solution, syrup or suspension, while for parenteral administration, as transdermal or hypodermic injections, or injections into abdominal cavity or muscles.

BEST MODE FOR CARRYING OUT THE INVENTION

Now, the present invention is described with reference to Examples, Preparation Examples and Experimental Examples. However, it should be noted that the present invention is not restricted to those examples.

EXAMPLE 1

Isolation and Purification of Asiaticoside and Asiatic Acid in Large Scale

Quantitative extract (5 g) of *Centella asiatica* was directly separated by column chromatography (silica gel, 230–400 mesh; dichloromethane/methanol=10/1) to obtain asiatic acid (1.5 g), madecassic acid (1.4 g) and mixture (2.0 g) of asiaticoside and madecassoside. The obtained mixture was dissolved in minimum amount of 60% methanol, in a water bath at 100° C., and then cooled at room temperature to give pure asiaticoside as needle-like crystalline.

(m.p.: 230–240° C.)

Separately, the extract (62 g) was dissolved in methanol (700 ml), and 5N sodium hydroxide solution (50 ml) was added thereto, and the resultant mixture was heated under reflux for 10 hours. The reaction mixture was concentrated under reduced pressure, neutralized, filtered and dried to obtain a mixture (2, 43 g) of asiatic acid and madecassic acid.

EXAMPLE 2

Preparation of 3,23-O-isopropylidene asiatic acid (3)

The mixture (12 g) of asiatic acid and madecassic acid, and p-toluenesulfonic acid (200 mg) were dissolved in anhydrous DMF (100 ml), and 2,2-dimethoxypropane (5 ml) was added thereto by injection. The resultant mixture was stirred at room temperature for 14 hours, and then neutralized and concentrated under reduced pressure to remove the solvent. After extracting, washing and drying, the residue was purified by column chromatography (dichloromethane:methanol=30:1) to obtain 8.04 g of 3,23-O-isopropylidene asiatic acid (3).

IR (neat): 3440, 1698, 1200 cm$^{-1}$

Mass (EI): m/e 528 (M$^+$), 513 (M$^+$-Me), 482 (M$^+$-HCOOME), 452, 424, 407, 248, 203, 189, 133

$^1$H-NMR (CDCl$_3$): δ0.75, 1.04, 1.06, 1.09, 1.45, 1.46 (each s, 3H), 0.85 (d, 3H, J=6.4 Hz), 0.95 (d, 3H, J=6.4 Hz), 2.18 (d, 1H, J=11.2 Hz), 3.32 (d, 1H, J=9.6 Hz), 3.46, 3.51(ABq, 2H, J=10.18 Hz), 3.78 (m, 1H), 5.24 (brt, 1H)

EXAMPLE 3

Preparation of Methyl 3,23-O-isopropylideneasiatate (4)

3,23-O-Isopropylidene asiatic acid (3) (5 g) was dissolved in ethyl ether, and ethereal solution of diazomethane was slowly added dropwise is thereto at 0° C. After stirring at room temperature for 1 hour, the reaction mixture was concentrated under reduced pressure to remove ether, and the residue was purified by column chromatography (hexane:ethyl acetate=3:1) to obtain 4.9 g of methyl 3,23-O-isopropylidene asiatate (4) (95%).

IR (neat): 3466, 1724, 1201 cm$^{-1}$

Mass (EI): m/e 542 (M$^+$), 527 (M$^+$-Me), 482 (M$^+$-HCOOME), 483, 467, 451, 407, 262, 203, 189, 133

$^1$H-NMR (CDCl$_3$): δ0.66, 0.97, 1.00, 1.02, 1.40, 1.39 (each s, 3H), 0.79 (d, 3H, J=6.4 Hz), 0.87 (d, 3H, J=6.0 Hz), 2.15 (d, 1H), 3.25 (d, 1H,J=9.6 Hz), 3.41 3.43 (ABq, 2H), 3.53 (s, 3H), 3.72 (m, 1H), 5.18 (brt, 1H).

EXAMPLE 4

Preparation of 3,23-O-alkylidene asiatic acid (5)

① $R_f$=H, $R_g$=H

Dimethyl sulfoxide (2.5 eq.) and trimethylsilyl chloride (2.5 eq.) were added to THF with stirring. Asiatic acid (2) obtained above (2.53 g, 5.18 mmol) was added thereto, and the mixture was heated under reflux and argon atmosphere for 3 days. The solvent was evaporated under reduced pressure and the residue was purified by column chromatography (dichloromethane:methanol=20:1) to obtain 2.01 g of pale yellow solid (yield: 79.45%).

$^1$H NMR(300 MHz, CDCl$_3$) δ0.75, 1.05, 1.08, 1.12 (each s, 3H), 0.85 (d, 3H, J=6.18 Hz), 0.95 (d, 3H, J=5.76 Hz), 2.19 (d, 1H, J=10.9 Hz), 3.04, 3.76 (ABq, 2H, J=10.11 Hz), 3.23 (d, 1H, J=10.23 Hz), 3.87 (dt, 1H, J=4.26 Hz, 10.02 Hz), 4.95 (d,d, 2H, J=5.9 Hz), 5.24 (t, 1H)

② $R_f$=H, $R_g$=CH$_3$

Asiatic acid (255 mg, 0.52 mmol) obtained above was dried over p-toluenesulfonic acid under reduced pressure. Then the compound was dissolved in anhydrous THF, and CH$_3$CH(OEt)$_2$ (0.15 ml) was added dropwise thereto, and the resultant mixture was stirred at room temperature for 2 hours. To the reaction mixture, saturated solution of sodium carbonate was added by injection, and the solvent was removed by evaporation under reduced pressure. The residue was diluted with ethyl acetate, washed and dried, and purified by column chromatography (dichloromethane:methanol=20:1) to obtain 178 mg of the title compound (yield: 66.2%).

IR (neat) 2926, 1695 cm$^{-1}$

Mass (EI) m/e 514 [M$^+$]

$^1$H NMR (300 MHz, CDCl$_3$) δ5.14 (t, 1H), 4.64 (qt, 1H, J=4.92 Hz), 3.75 (m, 1H), 3.63, 2.97 (ABq, 2H, J=10.1 Hz), 3.17 (d, 1H, J=10.4 Hz), 0.98, 0.95, 0.65 (each s, 3H), 0.85 (d, 3H, J=5.49 Hz), 0.75 (d, 3H, J=6.39 Hz)

③ $R_f$=H, $R_g$=C$_6$H$_5$

Excepting from substituting C$_6$H$_5$CH(OMe)$_2$ for CH$_3$CH(OEt)$_2$, the same procedure as Example 4② was performed (yield:32.1%).

IR (neat) 3437, 1696 cm$^{-1}$

Mass (EI) m/e 576 [M$^+$]578

$^1$H NMR (300 MHz, CDCl$_3$) δ7.52~7.49 (m, 2H), 7.37~7.35(m, 3H), 5.53(s, 1H), 5.24(t, 1H), 3.90, 3.30(ABq, 2H, J=10.11 Hz), 3.47(d, 1H, J=10.47 Hz), 2.18(d, 1H, J=11.46 Hz), 1.19, 1.09, 4.07, 0.77 (each s, 3H), 0.93 (d, 3H, J=6.09 Hz), 0.85 (d, 3H, J=6.33 Hz)

④ $R_f$=CH$_3$, $R_g$=C$_2$H$_5$

Excepting from substituting C$_2$H$_5$COCH$_3$ for CH$_3$CH(OEt)$_2$, the same procedure as Example 4② was performed (yield:58.96%).

IR (neat) 3436, 1694 cm$^{-1}$

Mass (EI) m/e 542 [M$^+$]

$^1$H NMR (300 MHz, CDCl$_3$) δ5.18 (t, 1H), 3.68, 3.47 (ABq, 2H, J=4.26 Hz), 3.48 (d, 1H, J=7.05 Hz), 2.12(d, 1H,J=10.65 Hz), 0.97, 0.89, 0.69 (each s, 3H)

⑤ $R_f$=CH$_3$, $R_g$=C$_3$H$_7$

Excepting from substituting C$_3$H$_7$COCH$_3$ for CH$_3$CH(OEt)$_2$, the same procedure as Example 4② was performed (yield:43.01%).

IR (neat) 3369, 2928, 1694 cm$^{-1}$

Mass (EI) m/e 558 [M$^+$+2]

$^1$H NMR(300 MHz, CDCl$_3$) δ5.18(t, 1H), 3.79~3.75(m, 1H), 3.18 (d, 1H, J=10.23 Hz), 3.67, 2.98 (ABq, 2H, J=9.8 Hz), 2.12 (d, 1H, J=10.65 Hz), 1.05, 1.01, 0.98, 0.69 (each s, 3H), 0.88 (d, 3H, J=5.55 Hz), 0.79 (d, 3H, J=6.39 Hz)

⑥ $R_f$-$R_g$=—(CH$_2$)5—

Excepting from substituting cyclohexanone for CH$_3$CH(OEt)$_2$, the same procedure as Example 4② was performed.

Mass (EI) m/e $^1$H NMR (300 MHz, CDCl$_3$) δ0.77, 0.96, 1.07 (each s, 3H), 0.85 (d, 3H, J=6.33 Hz), 2.18 (d, 1H, J=11.46 Hz), 3.24 (d, 1H, J=9.51 Hz), 3.41, 3.59 (ABq, 2H, J=10.47 Hz), 3.76 (dt, 1H, J=8.54 Hz), 5.23 (t, 1H)

EXAMPLE 5

Preparation of octyloxymethyl 3,23-O-alkylidene asiatate(6)

① $R_f$=H, $R_g$=H

The compound 5(258.4 mg, 0.52 mmol) obtained in Example 4① above was dissolved in anhydrous dichloromethane. Diisopropylethylamine(0.18 ml) was added thereto and stirred at room temperature for 10 minutes. At 0° C., chloromethyloctyl ether(0.1 ml) was added dropwise thereto and stirred for 5 minutes. Methanol was added thereto and the residue was refined by column chromatography (dichloromethane:methanol=30:1) to obtain 138 mg of white solid (yield: 41.6%).

$^1$H NMR (400 MHz, CDCl$_3$) δ0.76, 1.05, 1.09, 1.13 (each s, 3H), 0.88 (d, 3H, J=5.6 Hz), 0.95 (d, 3H, J=6.36 Hz), 2.25 (d, 1H, J=10.8 Hz), 3.04, 3.76 (ABq, 2H, J=10.0 Hz), 3.22 (d, 1H, J=10.8 Hz), 3.58 (m, 2H), 4.94 (d,d, 2H, J=6.0 Hz), 5.21, 5.24 (ABq, 2H, J=5.88 Hz), 5.26 (t, 1H)

② $R_f$=H, $R_g$=CH$_3$

Excepting from substituting the compound 5 obtained in Example 4② for the compound 5 obtained in Example 4① above, the same procedure as Example 5① was performed.

IR (neat) 3481, 2927, 1732 cm$^{-1}$

Mass (EI) m/e 656 [M$^+$]

$^1$H NMR (300 MHz, CDCl$_3$) δ5.22 (t, 1H), 5.20, 5.17 (ABq, 2H,J=6.21 Hz), 4.69 (qt, 1H, J=4.95 Hz), 3.84~3.77 (m, 1H), 3.69, 3.03(ABq, 2H, J=10.07 Hz), 3.55 (m, 2H), 2.22 (d, 1H, J=11.16 Hz), 1.05, 1.00, 0.95, 0.72 (each s, 3H), 0.84 (d, 3H, J=2.55 Hz), 0.82 (d, 3H, J=219 Hz)

③ $R_f$=H, $R_g$=C$_6$H$_5$

Excepting from substituting the compound 5 obtained in Example 4③ for the compound 5 obtained in Example 4① above, the same procedure as Example 5① was performed (yield:23.8%).

IR (neat) 3697, 1730 cm$^{-1}$

Mass (EI) m/e 719 [M$^+$+1]

④ $R_f$=CH$_3$, $R_g$=C$_2$H$_5$

Excepting from substituting the compound 5 obtained in Example 4④ for the compound 5 obtained in Example 4① above, the same procedure as Example 5① was performed (yield:58.96%).

IR (neat) 3469, 1733 cm$^{-1}$

Mass (EI) m/e 684 [M$^+$]

$^1$H NMR (300 MHz, CDCl$_3$) δ5.16 (t, 1H), 5.14, 5.11 (ABq, 2H, J=6.29 Hz), 3.68(m,1H), 3.48 (m, 2H,), 3.24 (d, 1H, J=9.57 Hz), 2.16(d, 1H,J=11.5 Hz), 1.00, 0.96, 0.91, 0.66 (each s, 3H), 0.84(d,1H,J=5.55 Hz), 0.76(d,1H,J=5.73 Hz)

⑤ $R_f$=CH$_3$, $R_g$=C$_3$H$_7$

Excepting from substituting the compound 5 obtained in Example 4⑤ for the compound 5 obtained in Example 4① above, the same procedure as Example 5① was performed (yield:80.2%).

IR (neat) 3468, 2927, 1729 cm$^{-1}$

Mass (EI) m/e 698 [M$^+$]

$^1$H NMR (400 MHz, CDCl$_3$) δ5.26~5.20 (m, 2H), 5.10 (t, 1H), 3.87~3.84 (m, 1H), 3.60~3.56 (m, 2H), 2.27 (d, 1H), 1.08, 1.07, 1.03, 0.76 (each s, 3H), 0.94 (d, 3H, J=5.84 Hz), 0.87 (d, 3H, J=5.4 Hz)

⑥ $R_fR_g$=—(CH$_2$)$_5$—

Excepting from substituting the compound 5 obtained in Example 4⑥ for the compound 5 obtained in Example 4① above, the same procedure as Example 5① was performed (yield: 34%).

Mass (EI) m/e 710 [M$^+$], 667, 596, 567, 522, 521

$^1$H NMR (400 MHz, CDCl$_3$) δ0.75, 0.95, 1.03 (each s, 3H), 0.87 (d, 3H, J=5.86 Hz), 1.09 (d, 3H, J=3.9 Hz), 2.10 (d, 1H, J=4.40 Hz), 3.35 (d, 1H, J=9.77 Hz), 3.48, 3.52 (ABq, 2H, J=11.24 Hz), 3.58 (m, 2H), 3.8 (m, 1H), 5.21, 5.24 (dd, 2H, J=5.86 Hz), 5.26 (t, 1H)

EXAMPLE 6

Preparation of methyl 3,23-O-isopropylidene-2-O-[(methylthio)thiocarbonyl]asiatate(7)

Sodium hydride(60% dispersion of inorganic oil, 18.3 mg, 0.46 mmole), imidazole(2 mg) and tetrahydrofuran(2 ml) were added to methyl 3,23-O-isopropylidene asiatate (4) (50 mg, 0.092 mmole) and the resultant mixture was stirred for 30 minutes. Carbon disulfide(0.2 ml, excessive amount) was added thereto and refluxed for 2 hours. Methyl iodide (0.1 ml, excessive amount) was added thereto and heated under reflux again for 1 hour. The reactant mixture was treated with water and the solvent was removed under reduced pressure. After extracting, washing and drying the residue was refined by column chromatography (hexane:ethyl acetate=10:1) to obtain 56 mg of white solid (yield: 96%).

IR (neat): 1723, 1233, 1057 cm$^{-1}$ $^1$H NMR (CDCl$_3$) δ5.78(1H,m), 5.24(1H,bt), 3.80(1H,d, J=10 Hz), 3.60(3H,s), 3.54, 3.58(2H,dd,J=7.2 Hz), 2.51(3H, s), 2.23(1H,d,J=11.2 Hz), 0.94(3H,d, J=5.2 Hz), 0.84(3H,d, J=6 Hz), 0.73, 1.09, 1.11, 1.14, 1.41, 1.45 (each 3H,s).

EXAMPLE 7

Preparation of methyl 2-deoxy-3,23-O-isopropylidene asiatate(8)

A catalytic amount of AIBN and benzene(10 ml) were added to xanthate compound (7)(202 mg, 0.32 mmole) obtained above. Tributyltin hydride(0.26 ml, 0.96 mmole) was added thereto with the resultant heated under reflux and stirred for 1 hour and a half. The reactant mixture was concentrated under reduced pressure and the solvent was removed. The obtained residue was refined by column chromatography(hexane:ethyl acetate=10:1) to obtain 168 mg of white solid (yield: 100%). The product was recrystallized with hexane to yield needle-like crystalline.

IR (neat): 1724 cm$^{-1}$

MS (EI): 527(M$^+$+1), 512, 407, 262, 203, 133.

$^1$H NMR (CDCl$_3$) δ5.25(1H,bt), 3.60(3H,s), 3.52(1H,t), 3.44, 3.54(2H,dd,J=10 Hz), 2.23(1 H,d,J=11.2 Hz), 0.94 (3H, d, J=5.6 Hz), 0.86(3H,d,J=6.4 Hz), 0.73, 0.97, 1.07, 1.09, 1.42, 1.45(each 3H,s)

EXAMPLE 8

Preparation of methyl 2-deoxyasiatate(9)

Tetrahydrofuran(10 ml) and 1N HCl solution(1 ml) were added to the compound(8) (460 mg, 0.87 mmole) obtained above and stirred at room temperature for 5 hours. The solvent was totally removed by distillation under reduced pressure. The obtained residue was refined by column chromatography(hexane:ethyl acetate=3:2) to obtain 402 mg of white solid (yield: 95%). The crude product obtained was recrystallized with ethyl acetate to yield needle-like crystalline.

IR (neat): 3400, 1724 cm$^{-1}$
MS (EI): 486(M$^+$), 426, 262, 203, 133

EXAMPLE 9

Preparation of 2-deoxyasiatic acid (10)

LiI-3H$_2$O (450 mg, 2.39 mmole) and 2,4,6-colidine(5 ml) was added to methyl 2-deoxyasiatate (9) (38 mg, 0.78 mmole) and heated under reflux for 10 hours. The flask was covered with aluminum foil to block light during reflux. The reactant solution was concentrated under reduced pressure to remove collidine. The obtained residue was refined by column chromatography(dichloromethane:methanol=20:1) to obtain pale yellow solid (yield: 99%). The product obtained was recrystallized with methanol to yield 280 mg of needle-like crystalline(yield: 76%).

IR (KBr): 3436, 1693 cm$^{-1}$
MS (EI): 472(M$^+$), 426, 248, 203, 133
$^1$H NMR (CDCl$_3$+pyridine-d$_5$) δ5.21(1H,bt,J=2.8 Hz,3.6 Hz), 3.60(1H,t,J=7.2 Hz,8.2 Hz), 3.36, 3.70 (2H,dd,J=10.0 Hz), 2.21(1H,d,J=11.2 Hz).

EXAMPLE 10

Preparation of 2-deoxy-3,23-O-isopropylidene asiatic acid (11)

Excepting from substituting the compound 10 for the mixture of asiatic acid and madecassic acid, the same procedure as Example 2 was performed (yield:59.9%).

IR (neat) 2928, 1697 cm$^{-1}$
$^1$H NMR (400 MHz, CDCl3) δ5.25 (d, 1H), 3.52 (t, 1H), 2.17 (d, 1H), 1.44, 1.40, 1.10, 1.04, 0.98, 0.78 (each s, 3H), 0.95 (d, 3H, J=6.4 Hz), 0.87 (d, 3H, J=6.4 Hz)

EXAMPLE 11

Preparation of octyloxymethyl 2-deoxy-3,23-O-isopropylidene asiatate(12, R$_e$=octyloxymethyl)

Excepting from substituting the compound 11 for the compound 5 in Example 5①above, the same procedure as Example 5① was performed (yield:53.9%).

IR (neat) 2929, 1733 cm$^{-1}$
Mass (EI) m/e 654 [M$^+$]
$^1$H NMR (500 MHz, CDCl$_3$) δ5.17 (t, 1H), 5.14, 5.12 (ABq, 2H, J=6.02 Hz), 3.49~3.48 (m, 2H), 3.46, 3.34(ABq, 2H,J=6.17 Hz), 2.15 (d, 1H), 1.35, 1.32, 1.01, 0.96, 0.67 (each s, 3H), 0.87 (d, 3H, J=7.04 Hz),

EXAMPLE 12

Preparation of ethyloxymethyl 2-deoxy-3,23-O-isopropylidene asiatate(12, R$_e$=ethyloxymethyl)

Excepting from substituting the compound 11 for the compound 5 in Example 5① and substituting chloromethylethyl ether for chloromethyloctyl ether, the same procedure as Example 5① was performed (yield:46%).

IR (neat) 2929, 1733 cm$^{-1}$
Mass (EI) m/e 570 [M$^+$]
$^1$H NMR (500 MHz, CDCl$_3$) δ5.16 (t, 1H), 5.16 (s, 2H), 3.60, 3.58(ABq, 2H, J=1.36 Hz), 3.45~3.35 (m, 3H), 2.15 (d, 1H), 1.45, 1.38, 1.34, 1.04, 0.98, 0.70 (each s, 3H), 0.88 (d, 31H, J=6.32 Hz), 0.79 (d, 3H, J=2.24 Hz)

EXAMPLE 13

Preparation of tetrahydropyranyl 2-deoxy-3,23-O-isopropylidene asiatate (12, R$_e$=2-tetrahydropyranyl)

The compound 11(133 mg, 0.26 mmol) and pyridinium paratoluene sulfonate(catalytic amount) were dissolved in anhydrous dichloromethane. Dihydropyrane(0.07 ml) was added dropwise thereto and stirred at room temperature for 40 hours. The resultant was neutralized and the solvent was removed under reduced pressure. After extracting, washing and drying, the residue was refined by column chromatography (hexane:ethyl acetate=8:1) to 73 mg of the compound (12, R$_e$=2-tetrahydropyranyl) (yield:47.2%).

IR (neat) 2945, 1733 cm$^{-1}$
$^1$H NMR (400 MHz, CDCl$_3$) δ5.96(t, ½H), 5.92(t, ½H), 5.28(t, ½H), 5.26 (t, ½H), 3.88 (t, 1H), 3.67 (t, 1H), 3.52 (t, 2H), 3.46 (t, 2H), 1.45, 1.42, 1.11, 1.05, 0.96 (each s, 3H), 0.87 (d, 3H, J=6.4 Hz)

EXAMPLE 14

Preparation of methyl 2-O-octyloxymethyl-3,23-O-isopropylidene asiatate (13)

Excepting from substituting the compound 4 for the compound 5 in Example 5①, the same procedure as Example 5① was performed.

IR (neat) 2927, 1728 cm$^{-1}$
Mass (EI) m/e 684 [M$^+$]
$^1$H NMR (500 MHz, CDCl$_3$) δ5.18 (t, 1H), 4.73, 4.62 (ABq, 2H, J=6.72 Hz), 3.70~3,65 (m, 1H), 3.53 (s, 3H), 3.35 (d, 1H, J=9.76 Hz), 1.36, 1.33, 1.02, 1.01, 0.96, 0.66 (each s, 3H), 0.87 (d, 3H, J=6.18 Hz), 0.79 (d, 3H, J=6.46 Hz)

EXAMPLE 15

Preparation of methoxymethyl 3,23-O-isopropylidene asiatate (14, R$_e$=methoxymethyl)

Excepting from substituting the compound 3 for the compound 5 in Example 5① and substituting chloromethylmethyl ether for chloromethyloctyl ether, the same procedure as Example 5① was performed (yield: 19%).

mp. 104–112° C.
$^1$H NMR (300 MHz, CDCl$_3$): δ0.77, 1.04, 1.08, 1.11, 1.45, 1.46(each s, 3H), 0.87 (d, 3H, J=6.3 Hz), 0.96(d, 3H, J=5.7 Hz), 2.27 (d, 1H, J=11.1 Hz), 3.32 (d, 1H, J=9.6 Hz), 3.45 (s, 3H), 3.47 (d, 1H, 9.6 Hz), 3.55 (d, 1H, 9 Hz), 3.79 (m, 1H), 5.17 (d, 1H, 6 Hz), 5.20 (d, 2H, J=6 Hz), 5.28 (t, 1H, J=3.5 Hz)
IR (KBr) cm$^{-1}$ 3500, 2950, 1740, 1450, 1380. 1065, 925, 860
[α]$_0^{23}$=+10.4° (c=0.2, CHCl$_3$)

EXAMPLE 16

Preparation of ethoxymethyl 3,23-O-isopropylidene asiatate (14, R$_e$=ethoxymethyl)

Excepting from substituting the compound 3 for the compound 5 in Example 5① and substituting chloromethylethyl ether for chloromethyloctyl ether, the same procedure as Example 5① was performed (yield:46%).

IR (neat): 3468, 1734 cm$^{-1}$
MS (EI) m/z: 586 (M$^+$)
$^1$H NMR (400 MHz, CDCl$_3$) δ5.27 (t,1H), 5.23 (s,2H), 3.74–3.82 (m,1H), 3.66 (q,2H,J=7.6 Hz), 3.53, 3.44 (ABq, 2H), 3.32 (d, 1H, J=9.6 Hz), 2.25 (d , 1H), 1.46, 1.44, 1.10 (ABq, 2H), 1.07, 1.03, 0.76 (each s, 3H), 1.22 (t, 3H, J=6.8 Hz), 0.95 (d, 3H, J=5.6 Hz), 0.86 (d, 3H, J=6.4 Hz)

EXAMPLE 17

Preparation of methoxyethoxymethyl 3,23-O-isopropylidene asiatate (14, R$_e$=methoxyethoxymethyl)

Excepting from substituting the compound 3 for the compound 5 in Example 5① and substituting methoxyethoxymethyl chloride for chloromethyloctyl ether, the same procedure as Example 5① was performed (yield:25%).

mp. 76–79° C.

$^1$H NMR (300 MHz, CDCl$_3$): δ0.77, 1.04, 1.08, 1.11, 1.45, 1.46 (each s, 3H), 0.86 (d, 6.3 Hz, J=3 Hz), 0.96 (d, 3H, J=5.7 Hz), 2.2–0.9 (m, 21H), 2.26 (d, 1H, J=10.2 Hz), 3.32 (d, 1H, J=9.6 Hz), 3.39 (s, 3H), 3.47 (d, J=9.0 Hz), 3.52 (d, 1H, J=9.0 Hz), 3.55 (t, 2H, J=5.1 Hz), 3.77 (m, 1H), 3.77 (t, 2H, J=5.1 Hz), 5.26 (t, 1H, J=3.6 Hz), 5.28 (s, 2H)

IR (KBr) cm$^{-1}$ 3500, 2950, 1725, 1450, 1380, 1070, 940, 860

$[\alpha]_0^{24}$=+38.7° (c=0.1, CHCl$_3$)

EXAMPLE 18

Preparation of methoxymethyl 2-O-acetyl-3,23-O-isopropylideneasiatate(15, R$_e$=methoxymethyl)

The compound 14(R$_s$=methoxymethyl, 139 mg, 0.24 mmol) obtained above was dissolved in pyridine and stirred. Acetic anhydride(0.04 ml, 0.38 mmol) was added thereto and stirred for 2 days. The resultant was concentrated under reduced pressure, washed, dried and refined by column chromatography (dichloromethane:methanol=30:1) to 75 mg of white solid (yield:52%).

mp. 110–115° C.

$^1$H NMR(300 MHz, CDCl$_3$): δ0.77, 1.09, 1.11, 1.12, 1.41, 1.43, 2.01 (each s, 3H), 0.86 (d, 3H, J=6.3 Hz), 0.95 (d, 3H, J=6 Hz), 2.27 (d, 1H, J=10.8 Hz), 3.45 (s, 3H), 3.50 (d, 1H, J=9.6 Hz), 3.52 (d, 1H, J=9.6 Hz), 3.56 (d, 3H, J=9 Hz), 5.0 (m, 1H), 5.17 (d, 1H, J=6 Hz), 5.20 (d, 1H, J=6 Hz), 5.27 (t, 1H, J=3.5 Hz)

IR (KBr) cm$^{-1}$ 2950, 2740, 1450, 1240, 1080, 1025, 950, 800

$[\alpha]_0^{24}$=+43.6° (c=0.1, CHCl$_3$)

EXAMPLE 19

Preparation of ethoxymethyl 2-O-acetyl-3,23-O-isopropylideneasiatate(15, R$_e$=ethoxymethyl)

Excepting from substituting the compound 14 (R$_s$=ethoxymethyl) obtained for the compound 14 (R$_s$=methoxymethyl) used in Example 18, the same procedure as Example 18 was performed (yield:91%).

mp. 136–137° C.

$^1$H NMR (300 MHz, CDCl$_3$): δ0.85 (d, 3H, J=6.1 Hz), 0.95 (d,3H, J=5.7 Hz), 1.01, 1.06, 1.08, 1.41, 1.43, 2.01 (each s, 3H), 0.9–2.2 (m, 20H), 1.21 (t, 7.3 Hz), 2.26 (d, 1H, 11.1 Hz), 3.48 (d, 1H, J=9 Hz), 3.53 (d, 1H, J=9 Hz), 3.54 (d, 1H, J=10.7 Hz), 3.66 (q, 2H, J=7.3 Hz), 5.00 (dt, 1H, 4.3, 10.7 Hz), 5.23 (s, 2H), 5.26 (t, 1H, J=4.2 Hz)

$[\alpha]_0^{24}$=−0.66° (c=0.34, CCl$_4$)

EXAMPLE 20

Preparation of ethoxymethyl 2-O-ethoxymethyl-3, 23-O-isopropylideneasiatate (16)

Excepting from substituting the compound 3 for the compound 5 obtained in Example 5① above, and substituting chloromethylethyl ether for chloromethyloctyl ether, the same procedure as Example 5① was performed (yield: 19%).

mp. 68–70° C.

$^1$H NMR (300 MHz, CDCl$_3$): δ0.86 (d, 3H, J=6.3 Hz), 0.95 (d, 3H, J=5.7 Hz), 0.80, 1.05, 1.10, 1.41, 1.51 (each s, 3H), 0.9–2.2 (m, 20H), 1.22 (t, 3H, J=7.2 Hz), 2.26 (d, 1H, J=11.1 Hz), 3.35 (d, 1H, J=9 Hz), 3.39 (d, 1H, J=9 Hz), 3.46 (d, 1H, J=9.6 Hz), 3.60 (q, 2H, J=7.2 Hz), 3.76 (q, 2H, J=7.2 Hz), 3.80 (dt, 1H, 4.2, 9.6 Hz), 4.67 (s, 2H), 5.24 (s, 2H), 5.27 (t, 1H, J=3.6 Hz)

IR (KBr) cm$^{-1}$ 2950, 1715, 1450, 1380, 1020, 925, 860

$[\alpha]_0^{24}$=+33.1° (c=0.1 CHCl3)

EXAMPLE 21

Preparation of benzyloxymethyl 3,23-O-diacetyl asiatate (17)

Excepting from substituting the compound 3 for the compound 5 obtained in Example 5① and substituting chloromethylbenzyl ether for chloromethyloctyl ether, the same procedure as Example 5① was performed and then synthesized through acetylization (yield:45%).

$^1$H NMR (300 MHz, CDCl$_3$): δ0.75, 0.85, 0.99, 1.10, 2.04, 2.09 (each s, 3H), 0.89 (d, 3H, J=6.3 Hz), 0.9–2.2 (m, 21H), 2.27 (d, 1H, J=12.9 Hz), 3.57 (d, J=11.7 Hz), 3.83 (d, J=11.7 Hz), 3.90 (dt, 1H, 3.9, 10.2 Hz), 4.68 (s, 2H), 5.04 (d, 1H, J=10.2 Hz), 5.28 (t, 1H, J=3.6 Hz), 5.32 (s, 31H), 7.34 (s, 5H)

IR (neat) cm$^{-1}$ 2950, 2740, 1450, 1380, 1065, 925, 860, 800

$[\alpha]_0^{25}$ =+25.25° (c=0.1, CHCl$_3$)

EXAMPLE 22

Preparation of methyl 2-O-methanesulfonyl-3,23-O-isopropylideneasiatate (18)

Methyl 3, 23-O-isopropylidene asiatic acid (4) (354.7 mg, 0.65 mmole) was dissolved in dichloromethane(15 ml). Triethyl amine(82.4 mg, 0.72 mmole) and methanesulfonyl chloride(99.2 mg, 0.98 mmole) were added thereto and stirred at 0° C. for 3 hours under nitrogen atmosphere. After the reaction was finished, the solvent was removed. After extracting, washing and drying, the residue was refined by column chromatography (hexane:ethyl acetate=2:1) to 380 mg of pure the compound 18 as white solid (yield:93%).

$^1$H NMR (CDCl$_3$) δ5.24(1H, m), 4.69–4.62 (1H, m), 3.60 (3H, s), 3.57 (1H, d ,J=10.5 Hz), 3.53 (1H, d, J=10.5 Hz), 3.49 (1H, d, J=10.5 Hz), 3.01 (3H, s), 2.26–2.20 (1H, m), 2.23(1H, bs), 1.44 (3H, s), 1.40 (3H, s), 1.11 (3H, s), 1.09 (3H, s), 1.07 (3H, s), 0.94 (3H, d, J=6.0 Hz), 0.85 (3H, d, J=7.0 Hz), 0.72(3H,s)

EXAMPLE 23

Preparation of methyl 2-O-methanesulfonyl asiatate (19)

The compound 18(1.2 g, 1.92 mmole) obtained above was dissolved in methanol(30 ml). p-toluenesulfonic acid(480 mg, 2.52 mmole) was added thereto and refluxed for 10 minutes under nitrogen atmosphere. The reactant was neutralized, extracted, washed, dried and refined by column chromatography (hexane:ethyl acetate=1:1) to obtain 1.06 g of the pure compound 19 as colorless oil(yield: 94%).

$^1$H NMR (CDCl$_3$) δ5.24 (1H, m), 4.77–4.74 (1H, m), 3.69 (1H, d, J=10.5 Hz), 3.61 (3H,s), 3.44 (1H, d, J=10.5 Hz), 3.70 (1H, bs), 3.10 (3H, s), 1.08 (3H, s), 1.07 (3H, s), 0.95 (3H, s), 0.94 (3H, d, J=5.1 Hz), 0.85 (3H, d, J=6.5 Hz), 0.74 (3H, s)

EXAMPLE 24

Preparation of methyl 2,3-epoxyasiatate (20)

The compound 19(2.78 g, 4.77 mmole) obtained above was dissolved in methanol(60 ml). Potassium carbonate (1.32 g, 9.53 mmole) was added thereto and stirred at room temperature for 3 days under nitrogen atmosphere. After the reaction was finished, solvent was removed. After extracting, washing and drying, the residue was refined by column chromatography (hexane:ethyl acetate=2:1) to obtain 2.05 g of the pure compound 20 as white solid (yield: 89%).

m.p.: 230~234° C.

IR (KBr): 3400, 2920, 1730, 1430, 1450, 1200, 1040 cm$^{-1}$ $^1$H NMR (CDCl$_3$) δ5.27 (1H, m), 3.60 (3H, s), 3.56 (1H, m), 3.31 (1H, m), 3.27 (1H,m), 3.11 (1H, d, J=4.0 Hz), 1.12 (3H, s), 1.6 (3H, s), 0.96 (3H, s), 0.94 (3H, d, J=5.1 Hz), 0.86 (3H, d, J=6.4 Hz), 0.74 (3H, s)

EXAMPLE 25

Preparation of methyl 2β-iodo-2-deoxyasiatate(21)

The compound 20(24.5 mg, 0.05 mmol), LiI·3H$_2$O(98 mg, 10.3eq) were dissolved in THF(5 ml). AcOH(0.5 ml) was added thereto with stirring, and the resultant was reacted for 1 day under argon atmosphere. The resultant was diluted with water, extracted with ethyl acetate, washed with brine and 10% Na$_2$S$_2$O$_3$ solution, dried, and refined by column chromatography(hexane:ethyl acetate=3:1) to obtain 16.5 mg of colorless solid (yield: 53.3%).

$^1$H NMR (300 MHz, CDCl$_3$): δ0.74, 0.85, 1.02, 1.08 (each s, 3H), 0.86 (d, 3H, J=6.3 Hz), 0.94 (d, 3H, J=5.13 Hz), 2.24 (d, 1H, J=11.2 Hz), 3.42, 3.72 (ABq, 2H, J=12.7 Hz), 3.60 (s, 3H), 4.57 (dt, 1H), 5.25 (t, 1H)

Mass (EI) m/e 612 [M$^+$], 552, 467, 407, 349

EXAMPLE 26

Preparation of 3,23-O-methylidene-2-oxoasatic acid (22)

The compound 5(R$_f$=R$_g$=H, 1.1 g 2.2 mmole) and pyridinium dichromate(0.83 g, 2.2 mmole) were dissolved in anhydrous dichloromethane. Acetic anhydride (0.62 ml) was added thereto and heated under reflux for 2 hours. The reactant was diluted with ethyl acetate, filtrated and refined by column chromatography (dichloromethane:methanol= 20:1) to obtain the compound 23(0.32 g, yield 29.2%)

$^1$H NMR (300 MHz, CDCl$_3$) δ0.75, 1.02, 1.07, 1.13 (each s, 3H), 0.95 (d, 3H, J=5.9 Hz), 0.85 (d, 3H, J=6.3 Hz), 2.11–2.21 (m, 2H), 2.39 (d, 1H, J=12.7 Hz), 3.42, 3.84 (ABq, 2H, J=10.4 Hz), 4.10 (s, 1H), 4.69, 5.20 (ABq, 2H, J=5.9 Hz), 5.23 (t, 1H)

EXAMPLE 27

Preparation of Octyloxymethyl 3,23-O-methylidene-2-oxoasiatate(23)

Except from substituting the compound 22 for the compound 5 used in Example 5①, the same procedure as Example 5① was performed(yield: 44%).

$^1$H NMR (300 MHz, CDCl$_3$) δ0.78, 1.02, 1.10, 1.14 (each s, 3H), 0.87 (d, 3H, J=7.3 Hz), 0.95 (d, 3H, J=5.9 Hz), 2.13, 2.40 (ABq, 2H, J=12.7 Hz), 2.27 (d, 1H, J=11.5 Hz), 3.42, 3.84 (ABq, 2H, J=10.1 Hz), 3.58 (dt, 2H, J=5.6 Hz), 4.10 (s, 1H), 4.69, 5.24 (ABq, 2H, J=6.1 Hz), 5.20–5.25 (m, 2H), 5.25 (t, 1H)

Preparation Example 1

Tablets

| Active component | 2.5 mg |
| --- | --- |
| Lactose BP | 151.0 mg |
| Starch BP | 30.0 mg |
| Pre-gelatinized corn starch BP | 15.0 mg |

The active component was sieved, and mixed with lactose, starch and pre-gelatinized corn starch. Suitable amount of purified water was added thereto and the mixture was granulated. After drying, the granules were mixed with magnesium stearate and pressed to prepare tablets.

Preparation Example 2

Capsules

| Active component | 2.5 mg |
| --- | --- |
| Starch 1500 | 96.5 mg |
| Magnesium stearate BP | 1.0 mg |

The active component was sieved and mixed with vehicles. The mixture was filled in gelatin capsules.

Preparation Example 3

Injections

| Active component | 800 μg/ml |
| --- | --- |
| Dilute hydrochloric acid BP | until pH 3.5 |
| Injectable sodium chloride BP | maximum 1 ml |

Active component was dissolved in proper amount of injectable sodium chloride BP, and the pH of the resultant solution was adjusted to 3.5 by adding dilute hydrochloric acid BP. Then the volume of the solution was adjusted by using injectable sodium chloride BP, and the solution was thoroughly mixed. The solution was charged into 5 ml type1 ampoule made of transparent glass, and the ampoule was sealed under the upper lattice of air, by fusing the glass. Then the ampoule was sterilized by autoclaving at 120° C. for 15 minutes or more, to give injection.

Experimental Example 1

Protection Effect of Asiatic Acid Derivatives Against Galactosamine-induced Toxicity of Liver Cell To investigate the protection effect of the compounds of the formula 1 of this invention, i. e. 2-oxoasiatic acid, 2-methylasiatic acid, methyl 2α-acetoxyurs-12-en-23-al-3-on-28-oate, tetrahydropyranyl 3β,23-diacetoxyurs-12-en-28-oate, ethoxymethyl 2α-hydroxy-3β,23-isopropylidendioxyurs-12-en-28-oate, methyl 2,3-β-epoxy-12-en-23-carbomethoxyurs-28-oate, methyl 2,3-β-epoxy-12-en-23-benzamidours-28-oate, 1-ethoxyethyl asiatate and 2',3',4',6'-tetra-O-acetylglucosyl 2,3,23-tri-O-acetylurs-28-oate, against galactosamine-induced toxicity of liver cell, the following experiment was performed.

As experimental animals, male Wister rats weighing between 150~200 g were used. All rats were fasted during 18~24 h, and then the isolation of liver cells was performed by using the two-step collagenase flow-through method [D. M. Crisp and C. I. Pogson, *Biochem.*, 126, 1009 (1972)], which is a form that the Berry & Friend method [M. N. Berry and D. S. Friend, *J. Cell, Biol.*, 43, 5006 (1969)] is a little modified.

The isolated liver cells were incubated in a normal incubation medium for 1.5 h, and then more incubated in 1.5 mM galactosamine-containing incubation medium for 14 h to induce liver cells to get into the toxicity of galactosamine [Y. Kris, M. Tohkin and H. Hikino, *J. Nat. Prod.*, 46, 841 (1983)].

These liver cells getting into toxicity induced by said methods were incubated separately in the incubation mediums containing said compounds of 5 µg/ml and 50 µg/ml. Then, withdrawing the incubation medium, the activity of glutamic pyruvic transaminase (GPT) was determined by the Reitman-Frankel method [S. Reitman and S. Frankel, *Am, J. Cli. Pathol.*, 28, 56 (1957)]. The GPT value of healthy liver cell was defined as 100%, and that of liver cell getting into toxicity induced by said methods was defined as 0%. At the basis of said definition, the GPT values of liver cells recovered from galactosamine-induced toxicity by the compounds were converted into relative protections (%) to show the protection effect of liver cell against the toxicity by the compounds.

The results were showed in Table 1.

TABLE 1

Protection effects of asiatic acid derivatives against galactosamine-induced toxicity of liver cell at the concentration of 5 and 50 µg/ml.

| Compounds | Relative liver cell protection (%) | |
| --- | --- | --- |
|  | 5 µg/ml of compound concentration | 50 µg/ml of compound concentration |
| 2-Oxoasiatic acid | 15 | 62 |
| 2-Methylasiatic acid | 43 | 62 |
| Methyl 2 α-acetoxyurs-12-en-23-al-3-on-28-oate | 42 | 80 |
| Tetrahydropyranyl 3 β,23-diacetoxyurs-12-en-28-oate | 58 | 66 |
| Ethoxymethyl 2 α-hydroxy-3 β,23-isopropylidendioxyurs-12-en-28-oate | 66 | 45 |
| Methyl 2,3-β-epoxy-12-en-23-carbomethoxyurs-28-oate | 26 | 53 |
| Methyl 2,3-β-epoxy-12-en-23-benzamidours-28-oate | 38 | 40 |
| 1-Ethoxyethyl asiatate | 66 | 0 |
| 2',3',4',6'-Tetra-O-acetyl-glucosyl 2,3,23-tri-O-acetylurs-28-oate | 79 | 21 |

The asiatic acid derivatives of the formula 1 according to this invention showed the protection effect of 15~79% against galactosamine-induced toxicity of liver cell at their concentration of 5 µg/ml, and except for 1-ethoxyethyl asiatate, all of the test compounds showed the protection effect of 21~80% at their concentration of 50 µg/ml.

Experimental Example 2

Protection Effect of Asiatic acid Derivatives Against Carbon Tetrachloride-induced Toxicity of Liver Cell To investigate the protection effect of the compounds of the formula 1 of this invention against carbon tetrachloride-induced toxicity of liver cell, the following experiment was performed.

The experiment was performed in the same manner as in Experimental example 1, except that carbon tetrachloride was used by following method to induce liver cells to get into the toxicity.

The isolated liver cells were incubated in a normal incubation medium for 24 h, and then more incubated in 10 mM carbon tetrachloride-containing incubation medium for 1.5 h to induce liver cells to get into the toxicity of carbon tetrachloride [Y. Kiso, Y. Suzuki and H. Hikino, *Planta. Med.*, 49, 222 (1983)]. The results were showed in Table 2.

TABLE 2

Protection effects of asiatic acid derivatives against carbon tetrachloride-induced toxicity of liver cell at the concentration of 5 and 50 µg/ml.

| Compounds | Relative liver cell protection (%) | |
| --- | --- | --- |
|  | 5 µg/ml of compound concentration | 50 µg/ml of compound concentration |
| 2-Oxoasiatic acid | 30 | 44 |
| 2-Methylasiatic acid | 29 | 9 |
| Methyl 2 α-acetoxyurs-12-en-23-al-3-on-28-oate | 21 | 0 |
| Tetrahydropyranyl 3 β,23-diacetoxyurs-12-en-28-oate | 42 | 30 |
| Ethoxymethyl 2 α-hydroxy-3 β,23-isopropylidendioxyurs-12-en-28-oate | 15 | 5 |
| Methyl 2,3-β-epoxy-12-en-23-carbomethoxyurs-28-oate | 0 | 0 |
| Methyl 2,3-β-epoxy-12-en-23-benzamidours-28-oate | 0 | 23 |
| 1-Ethoxyethyl asiatate | 8 | 7 |
| 2',3',4',6'-Tetra-O-acetyl-glucosyl 2,3,23-tri-O-acetylurs-28-oate | 39 | 34 |

The asiatic acid derivatives of the formula 1 of this invention, except for methyl 2,3-β-epoxy-12-en-23-carbomethoxyurs-28-oate and methyl 2,3-β-epoxy-12-en-23-benzamidours-28-oate, showed protection effect of 8~42% against carbon tetrachloride-induced toxicity of liver cells at their concentration of 5 µg/ml. All of the test compounds, except for methyl 2α-acetoxyurs-12-en-23-al-3-on-28-oate and methyl 2,3-β-epoxy-12-en-23-carbomethoxyurs-28-oate, showed protection effect of 5~44% at their concentration of 50 µg/ml.

Experimental Example 3

Concentration Dependency of Protection Effect of Asiatic Acid Derivatives Against Galactosamine-induced Toxicity of Liver Cell To investigate concentration dependency of the protection effect of the compounds of the formula 1 of this invention, i. e. 2-oxoasiatic acid, 2-methylasiatic acid and methyl 2α-acetoxyurs-12-en-23-al-3-on-28-oate, against galactosamine-induced toxicity of liver cell, the experiment was performed in the same manner as in Experimental example 1, except that the compound concentrations tested were 1, 10, 50, 100 and 200 μM.

TABLE 3

Protection effects of asiatic acid derivatives against galactosamine-induced toxicity of liver cell according to the concentration of asiatic acid derivative compounds.

| Concentrations of compounds (μM) | Relative liver cell protection (%) | | |
|---|---|---|---|
| | 2-Oxoasiatic acid | 2-methylasiatic acid | Methyl 2 α-acetoxyurs-12-en-23-al-3-on-28-oate |
| 1 | 29.8 | 31.9 | 27.4 |
| 10 | 43.2 | 40.3 | 39.0 |
| 50 | 50.4 | 58.2 | 60.0 |
| 100 | 25.3 | 43.9 | 33.1 |
| 200 | 8.5 | 0.0 | 0.0 |

The higher the concentrations of 2-oxoasiatic acid, 2-methylasiatic acid and methyl 2α-acetoxyurs-12-en-23-al-3-on-28-oate were in the range of 1~50 μM, the greater were the protection effects of those. At the concentrations of 100 and 200 μM, however, the protection effects of them rapidly decreased.

Experimental Example 4

Concentration Dependency of Protection Effect of Liver Cell Against Carbon Tetrachloride-induced Toxicity by Asiatic Acid Derivatives To investigate the concentration dependency of the protection effect of the compounds of the formula 1 of this invention, i. e. 2-oxoasiatic acid, against carbon tetrachloride-induced toxicity of liver cell, the experiment was performed in the same manner as in Experimental example 2, except that the compound concentrations tested were 1, 10, 50, 100 and 200 μM.

TABLE 4

Protection effects of 2-oxoasiatic acid against carbon tetrachloride-induced toxicity of liver cell according to the concentration of 2-oxoasiatic acid.

| Concentrations of compound (μM) | Relative liver cell protection (%) |
|---|---|
| 1 | 1.6 |
| 10 | 5.0 |
| 50 | 3.3 |
| 100 | 30.9 |
| 200 | 48.1 |

At the concentration range of 1~200 μM, the higher the concentration of 2-oxoasiatic acid was, the greater was the protection effects of that.

Experimental Example 5

Safety Study Through Toxicity Test

Administering 2-oxoasiatic acid of various concentrations to male ICR mice weighing between 20~25 g by peritoneal injection, the toxicity of 2oxoasiatic acid was tested.

As a result, motor activity was decreased dose-dependently and pilo-erection, tachypnea and convulsion were induced dose-dependently. And the symptom of opisthotonus was showed at a fatal dose. Judging from the toxic symptoms and the time taken till death, 2-oxoasiatic acid was observed to induce the typical toxicity of central nervous system. The surviving mice showed rapid recovery and the weight of them did not change.

In the conclusion, $LD_{50}$ of 2-oxoasiatic acid for mouse administered by peritoneal injection was 0.75 g/kg, and that shows considerable safety of the compounds according to the present invention.

INDUSTRIAL APPLICABILITY

As can be seen from the Experimental Examples described above, the asiatic acid derivatives according to the present invention showed excellent liver protection or treatment effects.

What is claimed is:

1. A method of treating or preventing hepatotoxicity, said method comprising administering to a patient in need of such treatment, a therapeutically effective amount of a compound, or a pharmaceutically acceptable salt or ester thereof, represented by Formula 1

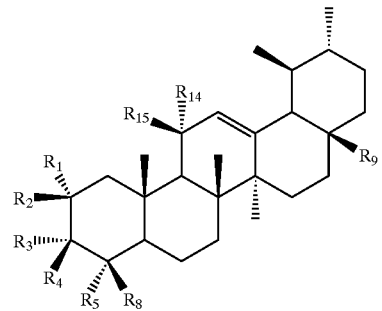

1 wherein:
$R_1$ is chosen from —H, a hydroxy group, a hydroxy group protected by an acetyl or benzoyl group, a methyl group, an ethyl group, a methoxy group, an ethoxy group, a vinyl group, an ethinyl group, a cyano group, an azide group, an ethoxymethyloxy group, an octyloxymethyloxy group, a methanesulfonyloxy group, a phenylthio group and a (methylthio)thiocarbonyloxy group, or $R_1$ and $R_2$ taken together may form an oxo group;

$R_2$ is chosen from —H, a methoxy group, an ethoxy group, a hydroxy group and a hydroxy group protected by an acetyl or benzoyl group, or $R_2$ and $R_4$ taken together may form an epoxy group;

$R_3$ is chosen from —H, a vinyl group, a methyl group, an ethyl group, a hydroxy group and a hydroxy group protected by an acetyl or benzoyl group or $R_3$ and $R_4$ taken together may form an oxo group;

$R_4$ is chosen from —H, a methyl group, an ethyl group, a vinyl group, a hydroxy group and a hydroxy group protected by an acetyl or benzoyl group;

$R_5$ is chosen from a methyl group, a hydroxymethyl group wherein the hydroxy group may be protected by an acetyl or benzoyl group, a t-butyldimethylsilyloxymethyl group, a carboxylic group, a carboxylic ester moiety, a carboxylic amide moiety and an aldehyde group, or $R_4$ and $R_5$ taken together may form —$OCR_6R_7OCH_2$—, wherein $R_6$ is chosen from —H, a lower alkyl group having 1–4 carbon atoms and a phenyl group;

$R_7$ is chosen from —H, a lower alkyl group having 1–4 carbon atoms and a phenyl group, or $R_6$ and $R_7$ taken together may form —$(CH_2)_5$;

$R_8$ is chosen from —H and a methyl group;

$R_9$ is chosen from —$CH_2COOR$ and —COOR, wherein

R is chosen from —H, a lower alkyl group having 1–4 carbon atoms, a 2-tetrahydropyranyl group, $CH(OR_{11})R_{10}$, $CH(OR_{13})CH_2R_{12}$, wherein $R_{10}$ is chosen from —H, a methyl group and an ethyl group;

$R_{11}$ is chosen from a lower alkyl group having 1–4 carbon atoms, an octyl group, a benzyl group, a methoxymethyl group and a methoxyethyl group;

$R_{12}$ is chosen from —H, a methyl group and an ethyl group; and $R_{13}$ is chosen from a methyl group and an ethyl group, or $R_{12}$ and $R_{13}$ taken together may form —$CH_2CH_2CH_2$—, a glucosyl or a rhamnosyl group, wherein the hydroxy group may be protected by an acetyl or benzoyl group, a hydroxymethyl group wherein the hydroxy group may be protected by an acetyl or a benzoyl group, a methanesulfonyloxymethyl group and a cyanomethyl group; and $R_{14}$ and $R_{15}$ are independently —H, or $R_{14}$ and $R_{15}$ taken together form an oxo group, with the provisos that:

when $R_1$ and $R_4$ are hydroxy, $R_2$ and $R_3$ are —H, $R_5$ is hydroxymethyl and $R_8$ is methyl, R is not —H or methyl and $R_{10}$ is not —H; and when $R_1$ is —OH, $R_2$ is —H, $R_3$ or $R_4$ form with $R_5$ —$OC(R_6)(R_7)OCH_2$—, and $R_6$ is methyl, R is not methyl, and a pharmaceutically acceptable carrier.

2. The method according to claim 1, wherein the hepatotoxicity is chemically-induced.

3. The method according to claim 1, wherein the compound represented by Formula 1 is selected from the group consisting of 2-oxoasiatic acid, 2-methylasiatic acid, methyl-2α-acetoxyurs-12-en-23-al-3-on-29-oate, tetrahydropyranyl-3β, 23-diacetoxyurs-12-en-28-oate, ethoxymethyl-2α-hydroxy-3,β,23-isopropylidendioxyurs-12-en-28-oate, methyl-2,3-β-epoxy-12-en-23-carbomethoxyurs-28-oate, methyl-2,3,-β-epoxy-12-en-23-benzamidours-28-oate, 1-ethoxyethyl asiatate, and 2',3',4',6'-tetra-O-acetylglucosyl 2,3,23-tri-O-acetylurs-28-oate.

* * * * *

UNITED STATES PATENT AND TRADEMARK OFFICE
CERTIFICATE OF CORRECTION

PATENT NO.   : 6,274,559 B1
DATED        : August 14, 2001
INVENTOR(S)  : Jew et al.

It is certified that error appears in the above-identified patent and that said Letters Patent is hereby corrected as shown below:

Column 28,
Line 16, delete "29" and insert therefore -- 28 --
Line 18, delete "3,β" and insert therefore -- 3β --

Signed and Sealed this

Fourteenth Day of May, 2002

Attest:

Attesting Officer

JAMES E. ROGAN
Director of the United States Patent and Trademark Office